United States Patent
Surti

(10) Patent No.: US 8,317,679 B2
(45) Date of Patent: Nov. 27, 2012

(54) ENDCAP FOR SAFELY DEPLOYING TISSUE ANCHORS

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 684 days.

(21) Appl. No.: 12/572,636

(22) Filed: Oct. 2, 2009

(65) Prior Publication Data

US 2010/0087707 A1  Apr. 8, 2010

Related U.S. Application Data

(60) Provisional application No. 61/103,042, filed on Oct. 6, 2008.

(51) Int. Cl.
| | |
|---|---|
| A61B 1/00 | (2006.01) |
| A61B 17/08 | (2006.01) |
| A61B 17/04 | (2006.01) |
| A61B 17/12 | (2006.01) |

(52) U.S. Cl. ..................... 600/104; 606/153; 606/144
(58) Field of Classification Search .................. 600/104, 600/201, 106, 103, 107, 127, 129; 606/228, 606/185, 153, 144
See application file for complete search history.

(56) References Cited

U.S. PATENT DOCUMENTS

| | | | |
|---|---|---|---|
| 5,304,184 | A | 4/1994 | Hathaway et al. |
| 5,476,469 | A | 12/1995 | Hathaway et al. |
| 5,562,688 | A | 10/1996 | Riza |
| 5,728,124 | A | 3/1998 | Cockburn et al. |
| 5,807,304 | A | 9/1998 | Cockburn |
| 5,824,010 | A | 10/1998 | McDonald |
| 5,908,428 | A | 6/1999 | Scirica et al. |
| 6,053,871 | A | 4/2000 | Cockburn |
| 6,290,674 | B1 | 9/2001 | Roue et al. |
| 6,328,727 | B1 | 12/2001 | Frazier et al. |
| 6,358,197 | B1 | 3/2002 | Silverman et al. |
| 6,425,887 | B1 | 7/2002 | McGuckin et al. |
| 6,712,804 | B2 | 3/2004 | Roue et al. |
| 7,060,078 | B2 | 6/2006 | Hathaway et al. |
| 7,115,110 | B2 | 10/2006 | Frazier et al. |
| 7,431,694 | B2 | 10/2008 | Stefanchik et al. |
| 7,481,826 | B2 | 1/2009 | Cichocki, Jr. |

(Continued)

OTHER PUBLICATIONS

Search Report/Written Opinion for PCT/US2009/059364 mailed Nov. 23, 2009.

*Primary Examiner* — John P Leubecker
*Assistant Examiner* — Ronald D Colque
(74) *Attorney, Agent, or Firm* — Brinks Hofer Gilson & Lione

(57) ABSTRACT

Medical systems, devices and methods are provided for manipulating tissue, such as for closing a perforation in an internal bodily lumen. One embodiment of a medical system generally includes an endoscope, an endcap attached to the distal end of the endoscope, a plurality of needles attached to the endcap, a stylet cap slidably disposed of the endcap, a plurality of stylets attached to the stylet cap, and a plurality of tissue devices. The plurality of needles define a plurality of needle lumens and the plurality of stylets project distally into the needle lumens. The plurality of tissue devices are positioned within the needle lumens, whereby translation of the stylet cap relative to the endcap causes the plurality of stylets to engage the plurality to tissue devices and eject them from the plurality of needles. The medical system may further include a protective tip slidably attached to the plurality of needles.

15 Claims, 6 Drawing Sheets

U.S. PATENT DOCUMENTS

| | | | |
|---|---|---|---|
| 7,575,548 B2 | 8/2009 | Takemoto et al. | |
| 7,618,426 B2 | 11/2009 | Ewers et al. | |
| 7,621,925 B2 | 11/2009 | Saadat et al. | |
| 7,704,264 B2 | 4/2010 | Ewers et al. | |
| 7,731,727 B2 | 6/2010 | Sauer | |
| 7,736,302 B2 | 6/2010 | Matsuno | |
| 7,780,687 B2 | 8/2010 | Heinrich et al. | |
| 2005/0137700 A1 | 6/2005 | Spence et al. | |
| 2005/0283246 A1* | 12/2005 | Cauthen et al. | 623/17.16 |
| 2006/0015006 A1 | 1/2006 | Laurence et al. | |
| 2006/0020274 A1 | 1/2006 | Ewers et al. | |
| 2006/0025654 A1 | 2/2006 | Suzuki et al. | |
| 2006/0253144 A1 | 11/2006 | Mikkaichi et al. | |
| 2006/0270906 A1 | 11/2006 | Matsuno | |
| 2007/0032796 A1* | 2/2007 | Chin-Chen et al. | 606/139 |
| 2007/0073319 A1* | 3/2007 | Mikkaichi et al. | 606/153 |
| 2007/0073320 A1* | 3/2007 | Mikkaichi et al. | 606/153 |
| 2007/0073321 A1* | 3/2007 | Mikkaichi et al. | 606/153 |
| 2007/0100376 A1* | 5/2007 | Mikkaichi et al. | 606/232 |
| 2007/0191886 A1 | 8/2007 | Dejima et al. | |
| 2007/0197864 A1 | 8/2007 | Dejima et al. | |
| 2007/0198000 A1 | 8/2007 | Miyamoto et al. | |
| 2007/0198074 A1* | 8/2007 | Dann et al. | 623/1.11 |
| 2007/0213702 A1 | 9/2007 | Kogasaka et al. | |
| 2007/0270752 A1 | 11/2007 | LaBombard | |
| 2007/0276424 A1* | 11/2007 | Mikkaichi et al. | 606/185 |
| 2008/0097152 A1 | 4/2008 | Stefanchik et al. | |
| 2008/0132948 A1 | 6/2008 | Surti et al. | |
| 2008/0183035 A1 | 7/2008 | Vakharia et al. | |
| 2008/0185752 A1 | 8/2008 | Cerwin et al. | |
| 2008/0208218 A1 | 8/2008 | Shiono | |
| 2008/0208219 A1 | 8/2008 | Suzuki | |
| 2008/0208220 A1 | 8/2008 | Shiono et al. | |
| 2008/0243148 A1 | 10/2008 | Mikkaichi et al. | |
| 2008/0294001 A1 | 11/2008 | Surti | |
| 2009/0005638 A1 | 1/2009 | Zwolinski | |
| 2009/0005800 A1 | 1/2009 | Franer et al. | |
| 2009/0018602 A1 | 1/2009 | Mitelberg et al. | |
| 2009/0082786 A1 | 3/2009 | Surti | |
| 2009/0088780 A1 | 4/2009 | Shiono et al. | |
| 2009/0125039 A1* | 5/2009 | Mikkaichi et al. | 606/144 |
| 2009/0149714 A1 | 6/2009 | Bonadio | |
| 2009/0204147 A1 | 8/2009 | Rahmani | |
| 2009/0259260 A1* | 10/2009 | Bentley et al. | 606/300 |
| 2009/0264905 A1* | 10/2009 | Funada | 606/146 |
| 2009/0281559 A1 | 11/2009 | Swain et al. | |
| 2009/0299135 A1 | 12/2009 | Spivey | |
| 2009/0326561 A1 | 12/2009 | Carroll, II et al. | |
| 2010/0010457 A1 | 1/2010 | Ewers et al. | |
| 2010/0010511 A1 | 1/2010 | Harris et al. | |
| 2010/0048990 A1 | 2/2010 | Bakos | |
| 2010/0056861 A1 | 3/2010 | Spivey | |
| 2010/0056862 A1 | 3/2010 | Bakos | |
| 2010/0094425 A1* | 4/2010 | Bentley et al. | 623/17.16 |
| 2010/0121140 A1 | 5/2010 | Hashiba et al. | |
| 2010/0145385 A1 | 6/2010 | Surti et al. | |
| 2010/0191267 A1 | 7/2010 | Fox | |
| 2010/0198005 A1 | 8/2010 | Fox | |
| 2010/0198149 A1 | 8/2010 | Fox | |
| 2010/0211086 A1 | 8/2010 | Ewers et al. | |
| 2010/0217151 A1 | 8/2010 | Gostout et al. | |
| 2010/0256679 A1 | 10/2010 | Ducharme | |

* cited by examiner

ENDCAP FOR SAFELY DEPLOYING TISSUE ANCHORS

CROSS-REFERENCE TO RELATED APPLICATIONS

This application claims the benefit of U.S. Provisional Application Ser. No. 61/103,042 filed on Oct. 6, 2008, entitled ""ENDCAP FOR SAFELY DEPLOYING TISSUE ANCHORS" the entire contents of which are incorporated herein by reference.

FIELD OF THE INVENTION

The present invention relates generally to endoscopic deployment of tissue anchors for manipulating tissue, e.g., closing perforations in the tissue.

BACKGROUND OF THE INVENTION

Perforations in bodily walls may be naturally occurring, or formed intentionally or unintentionally. In order to permanently close these perforations and allow the tissue to properly heal, numerous medical devices and methods have been developed employing sutures, adhesives, clips, staples and the like. One class of such devices is commonly referred to as tissue anchors (T-anchors) or visceral anchors. Exemplary tissue anchors are disclosed in U.S. Pat. No. 5,123,914 and U.S. application Ser. No. 11/946,565 filed Nov. 28, 2007, the entire contents of which are incorporated by reference herein. Such tissue anchors have been very successful in medical procedures requiring visceral wall mobilization or wall apposition.

Tissue anchors have also been successfully used in closing perforations, but are not without their drawbacks. For example, when a series of anchors are placed around a perforation, all of the individual sutures connected to the anchors must be collected and connected together. It can often be difficult to properly tension each of the individual sutures to ensure proper approximation of the tissue around the perforation and complete closure thereof. This is especially critical within the gastrointestinal tract, where the travel of bacteria laden fluids outside of the tract may cause unwanted and sometimes deadly infection.

BRIEF SUMMARY OF THE INVENTION

The present invention provides medical devices, systems and related methods for manipulating tissue, e.g. for closing a perforation in a bodily wall. One embodiment of a medical device, constructed in accordance with the teachings of the present invention, generally comprises an endcap, a plurality of needles, a stylet cap, a plurality of stylets, a plurality of tissue devices, and a protective tip. The endcap has a passageway sized to receive the endoscope therein. The plurality of needles are attached to the endcap and project distally therefrom. The plurality of needles define a plurality of needle lumens having distal ends for piercing tissue. The stylet cap is slidably disposed over the endcap. The plurality of stylets are attached to the stylet cap and project distally into the plurality of needle lumens. The plurality of tissue devices are positioned within the needle lumens, and translation of the stylet cap relative to the endcap causes the plurality of stylets to engage the plurality of tissue devices and eject them from the plurality of needles. The protective tip is slidably attached to the plurality of needles. The protective tip is operable between an extended position protecting the distal ends of the plurality of needles, and a retracted position exposing the distal ends.

According to more detailed aspects, in one embodiment of the device the plurality of needles are circumferentially spaced around the endcap and positioned radially outside of the passageway in the endcap. Preferably the plurality of needles includes at least four needles. The plurality of needles each have a length greater than the length of the protective tip. The endcap defines a plurality of endcap passageways slidably receiving the plurality of stylets. The protective tip defines a plurality of tip passageways slidably receiving the plurality of needles. The distal portions of the plurality of tip passageways may open laterally, wherein the needles each define a laterally opening slot that is circumferentially aligned with the laterally opening portion in each of the tip passageways. A suture may be slidably attached to at least one of the tissue devices, the suture extending between each of the tissue devices around the exterior of the protective tip.

In another embodiment, a medical system, constructed in accordance with the teachings of the present invention, generally includes an endoscope, an endcap attached to the distal end of the endoscope, a plurality of needles attached to the endcap, a stylet cap slidably disposed of the endcap, a plurality of stylets attached to the stylet cap, and a plurality of tissue devices. The plurality of needles define a plurality of needle lumens having distal ends for piercing the tissue, and are radially positioned outside of the passageway in the endcap. The plurality of stylets project distally into the plurality of needle lumens. The plurality of tissue devices are positioned within the needle lumens, whereby translation of the stylet cap relative to the endcap causes the plurality of stylets to engage the plurality to tissue devices and eject them from the plurality of needles.

According to more detailed aspects, the distal ends of the plurality of needles are positioned distally beyond the distal end of the endoscope and a distal end of the endcap. In some embodiments, the endcap defines a flange extending radially outwardly, the flange being sized and positioned to abut the stylet cap to limit the relative translation of the stylet cap and the endcap. The medical system may further include a protective tip slidably attached to the plurality of needles. The medical system may also include an elongated tip control member attached to the protective tip, an elongated endcap control member attached to the endcap, and an elongated stylet control member attached to the stylet cap. The tip control member, the endcap control member and stylet control member are translatable relative to one another and extend along the exterior of the endoscope. The stylet control member preferably defines a lumen slidably receiving the endcap control member and the tip control member.

One embodiment of a method of placing a plurality of tissue devices, in accordance with the teachings of the present invention, generally comprises providing a medical system such as the endoscope and one of the medical devices described above. The medical system is advanced through the bodily lumen to a location proximate the tissue with the protective tip in the extended position. The protective tip is operated to the retracted position and the tissue is pierced with a plurality of needles. The stylet cap is translated relative to the endcap to engage the plurality of tissue devices with the plurality of stylets and deploy the tissue devices. A protective tip is operated to the extended position and the medical system may be retracted through the bodily lumen.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
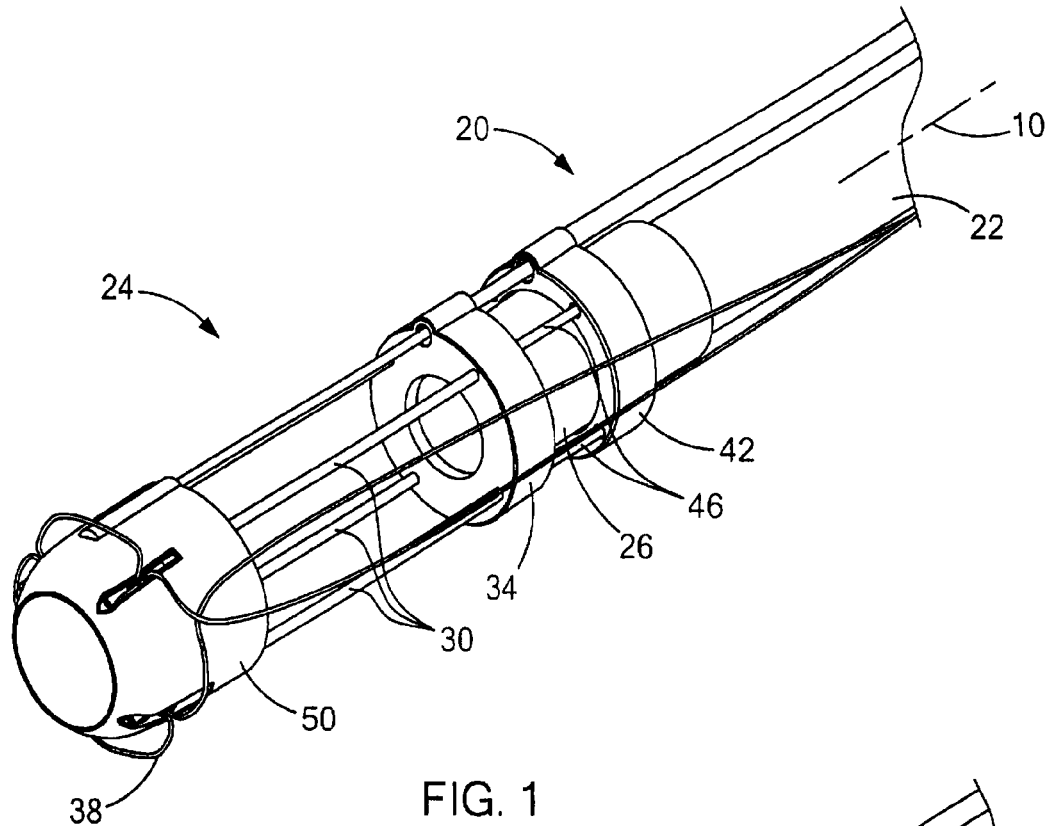
FIG. 1 is a perspective view of a medical device and system constructed in accordance with the teachings of the present invention.

In the present application, the terms "proximal" and "proximally" refer to a position, direction, or orientation that is generally towards a physician during a medical procedure, while the terms "distal" and "distally" refer to a position, direction, or orientation that is generally away from the physician and towards a target site within a patent's anatomy during a medical procedure. Thus, "proximal" and "distal" portions of a device or bodily region may depend on the point of entry for the procedure (e.g., percutaneously or laparoscopically or endoscopically).

Turning now to the figures, FIGS. 1-4 depict a medical system 20 for suturing closed a perforation 14 in tissue 12, constructed in accordance with the teachings of the present invention. The medical system 20 generally comprises an endoscope 22 and a medical device 24 adapted for use with the endoscope 22. The endoscope 22 generally defines a central axis 10 which extends in a longitudinal direction. The medical device 20 is selectively attachable to the endoscope 24, and the medical system 22 may be traversed through a bodily lumen of a patient to a desired location for performing procedures within the body, such as at a particular bodily wall or tissue. For example, the bodily lumen may be the esophagus and the bodily tissue may be the gastric wall, although the medical system 20 may be used with any bodily lumen or bodily cavity, and tissue, as will be understood by those skilled in the art. The endoscope 22 may generally be any medical scope known to those skilled in the art, and therefore may have various lengths, diameters, channels and functionality (e.g. ultrasound, imaging, torque-ability, etc).

Figure 3:
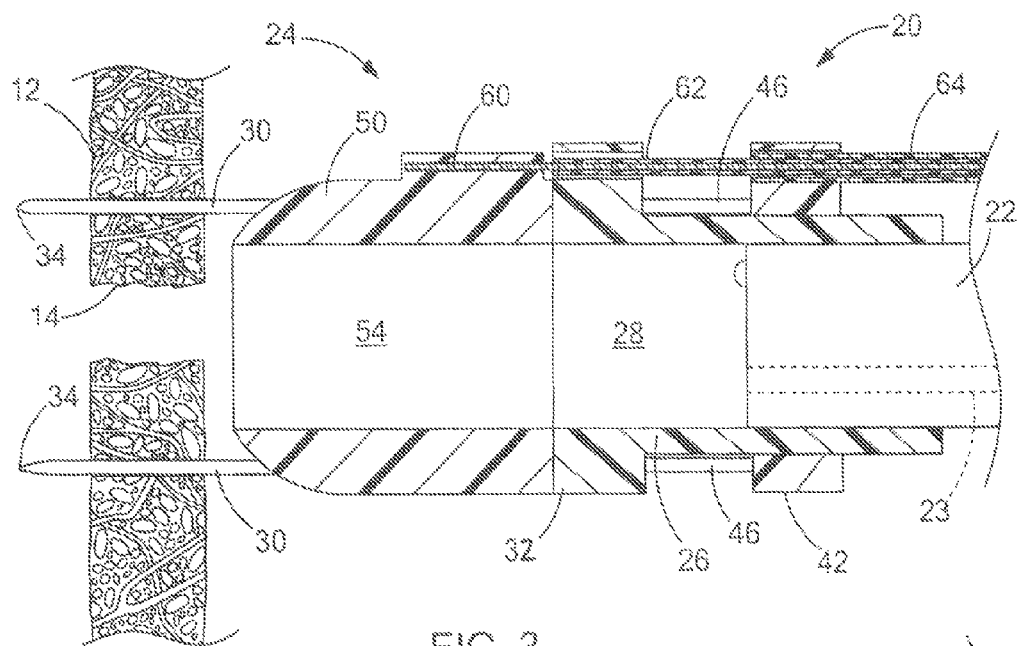
FIG. 3 is a cross-sectional view showing operation of the medical device and system depicted in FIG. 1.

The medical device 24 includes an endcap 26 defining an interior passageway 28 sized to be fitted on a distal end of the endoscope 22. The endcap 26 may be structured to frictionally engage the endoscope 22 for selective retention of the endcap 26 on the endoscope 22, although other means for connecting the endcap 26 to the endoscope 22 may be employed as is known in the art, including mechanical fasteners, adhesives, integral/unitary formation, etc. As shown in FIG. 3, the endcap 26 includes a passageway 28 sized to frictionally receive the endoscope 22 therein. The endoscope 22 and medical device 24 are therefore adapted to be traversed through the body of a patient in this connected configuration shown in the figures.

The medical device 24 further includes a plurality of needles 30 attached to the endcap 26. A distal end of the endcap 26 defines a flange 32 extending radially outwardly, and the proximal ends of the needles 30 are attached to or otherwise embedded in the flange 32 of the endcap 26. Each needle 30 includes a sharpened distal end 34 for piercing the tissue 12. Each needle 30 further defines a needle lumen 31 (FIG. 5) sized to slidably receive a tissue device such as the plurality of tissue anchors 36 shown in the figures. One or more sutures 38 are connected to the plurality of tissue anchors 36. Accordingly, the plurality of needles 30 include laterally opening slots 40 at their distal ends 34 through which the suture(s) 38 may extend, as is known in the art.

Notably, various types and designs of tissue anchors 54 may be employed in conjunction with the present invention, exemplary tissue anchors being disclosed in U.S. Pat. No. 5,123,914 and U.S. patent application Ser. No. 11/946,565. It will also be recognized that the medical system 20 and medical device 24 of the present invention may also be used in conjunction with other tissue devices such as staples, tacks and other known tissue engagement devices that are deployable through a need. Exemplary tissue staples and systems are disclosed in U.S. patent application Ser. No. 12/191,277, and exemplary tacks are disclosed in U.S. patent application Ser. No. 12/428,226. The disclosures of all of the above-identified patents/applications are hereby incorporated by reference in their entireties.

Figure 5:
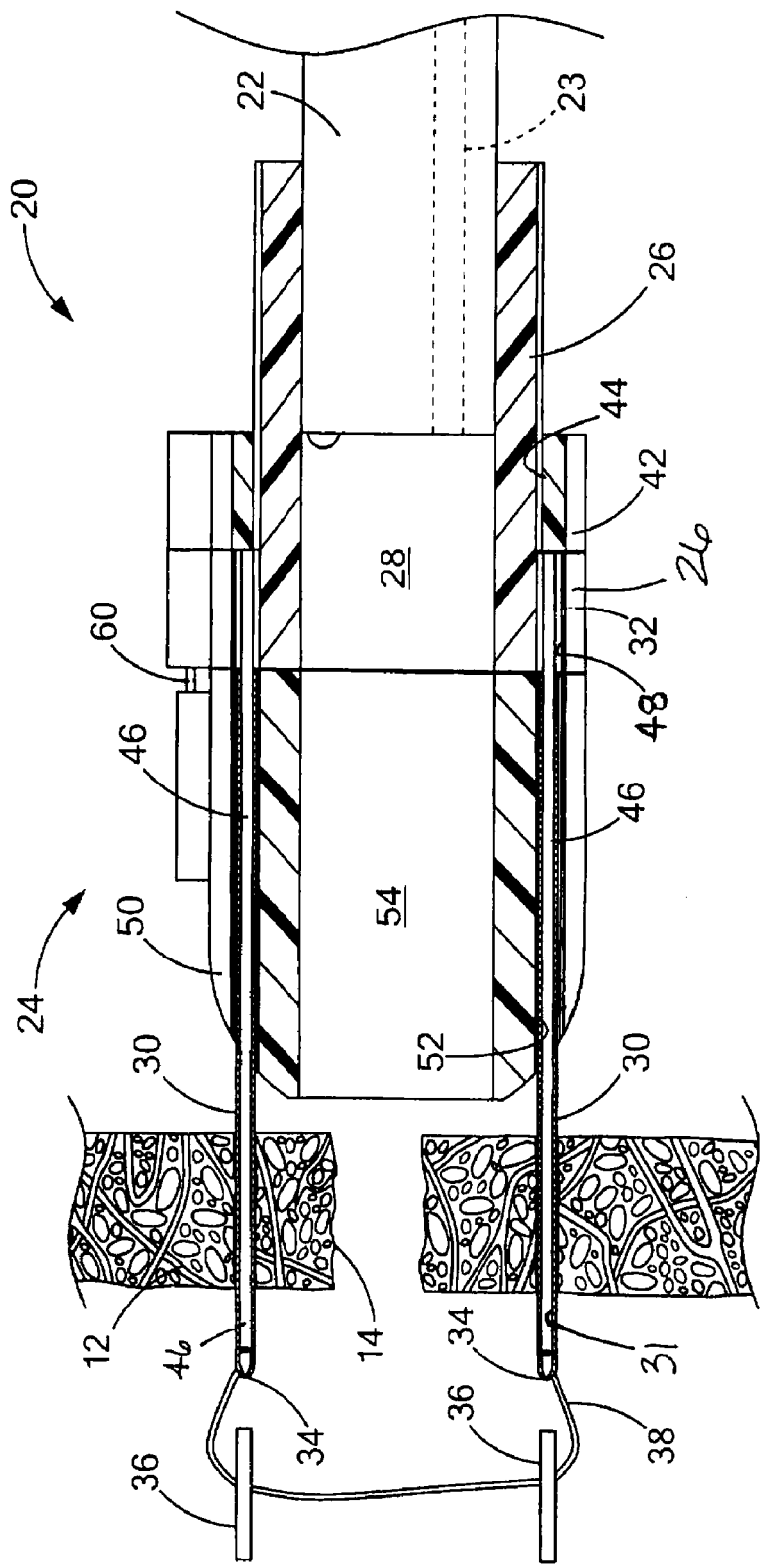
FIG. 5 is a cross-sectional view showing further operation of the medical device and system depicted in FIG. 1.

The medical device 24 further includes a stylet cap 42 slidably disposed over the endcap 26. As best seen in FIG. 3, the stylet cap 42 includes a passageway 44 sized to slidably receive the tubular endcap 26 therein. A plurality of stylets 46 are attached to the stylet cap 42 and project distally into the plurality of needles 30, and in particular into the needle lumens 31 (FIG. 5). It can be seen in FIG. 5 that the endcap 26, and in particular its flange 32, defines stylet passageways 48 aligned with the needles 30 for slidably receiving the stylets 46. It will also be recognized that the needles 30 may also extend into the stylet passageway 48.

Finally, the medical device 24 also includes a protective tip 50 slidably attached to the plurality of needles 30. As best seen in FIG. 5, the protective tip 50 defines a plurality of tip passageways 52 sized to slidably receive the plurality of needles 30. Further, the protective tip 50 defines an internal tip lumen 54. Preferably the tip lumen 54 has a diameter about equal to (that is, within 25%) the endcap passageway 28 such that the endoscope 22 may clearly visualize through both the endcap 26 and the protective tip 50. Likewise, medical instruments introduced through the working channel(s) 23 (FIGS. 3 and 5) of the endoscope 22 may be used beyond the distal end of the medical system 20, i.e. through the endcap 26 and through the protective tip 50. The protective tip 50 is operable between an extended position, shown in FIG. 1, and a retracted position, shown in FIG. 2. In the extended position, the protective tip 50 protects the distal ends 34 of the plurality of needles 30, and in the retracted position the protective tip 50 exposes the distal ends 34 for piercing tissue 12.

Figure 4:
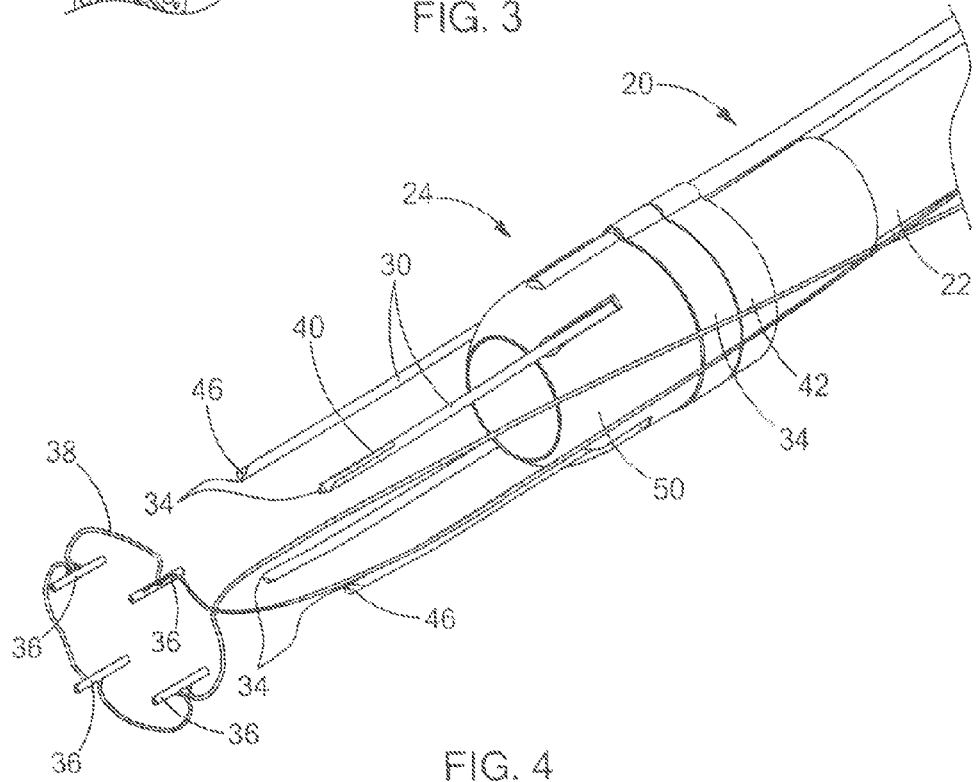
FIG. 4 is a perspective view showing further operation of the medical device and system depicted in FIG. 1.

The stylet cap 42 and the plurality of stylets 46 are operable to engage the plurality of tissue devices 36 contained within the plurality of needles 30 and deploy them by ejecting them out of the needles 30, as shown in FIG. 4. To operate and control the relative translation between the protective tip 50 and the endcap 26, and likewise to control the relative translation between the stylet cap 42 and the endcap 26, each are provided with elongated control members. As best seen in FIG. 3, the protective tip 50 includes a tip control member 60 attached thereto. The tip control member 60 may comprise a wire that is embedded in the protective tip 50 or otherwise attached thereto. The endcap 26 includes an endcap control member 62 comprising a catheter slidably receiving the tip control member 60. Finally, the stylet cap 42 includes a stylet control member 64 which also comprises a catheter. The stylet control member 64 is sized to slidably receive the endcap control member 62 (and hence the tip control member 60 as well). Each of the control members 60, 62, 64 are preferably structured to have sufficient longitudinal force transmission to allow for relative translation therebetween, as well as relative translation of the endcap 26, stylet cap 42 and protective tip 50. Where the control members comprise catheters or other tubular members, various plastics which may be employed such as polytetrafluorethylene (PTFE), expanded polytetrafluorethylene (EPTFE), polyethylene ether ketone (PEEK), polyvinylchloride (PVC), polycarbonate (PC), polyamide including Nylon™, polyimide, polyurethane, polyethylene (high, medium or low density), and elastomers such as Santoprene™, including multi-layer or single layer constructions with or without reinforcement wires, coils or filaments. Where the control members comprise a wire or the like, the control member may comprise a single solid wire, or multi-filament designs, including coiled, wound, braided or other designs known in the art.

In the depicted embodiment, the tip control member 60, endcap control member 62, and stylet control member 64 are concentrically arranged and extend proximally along the length of the endoscope 22. Accordingly, the control members 60, 62, 64 have a length generally similar to the length of the endoscope 22. The control members may be attached along their length to the endoscope 22, such as by using bands, tape, or the like. Likewise, the control members could be formed with the endoscope, or could be formed as part of an overtube or other introduction device. An appropriate handle may be employed at the proximal end of the medical system 20, the handle including various actuating portions to control the relative translation of the control members 60, 62, 64, as is known in the art. For example, the handle currently sold by Wilson-Cook (Cook Endoscopy) of Winston-Salem, N.C., in connection with its EchoTip® Endoscopic Ultrasound Needles, may be adapted for use with the medical system 20 and medical device 24 of the present invention, such as by connecting the main handle body to the endcap control member 62, connecting the outer slidable member to the stylet control member 64, and connecting the plunger (attached to the proximal end of the wire 60) to the tip control member 60.

Figure 2:
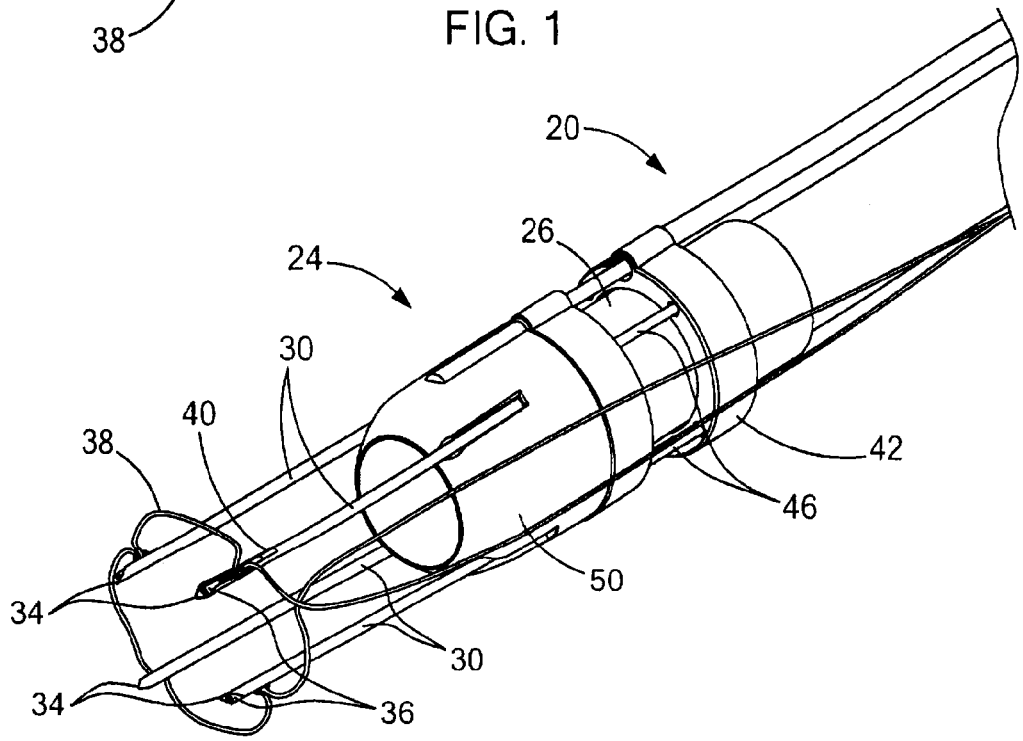
FIG. 2 is a perspective view showing operation of the medical device and system depicted in FIG. 1.

A method of deploying tissue devices such as the described tissue anchors 36, e.g. for closing the perforation 14, in accordance with the teachings present invention, will now be described. The method includes advancing the medical system 20 through the bodily lumen and proximate the tissue 12 with the protective tip 50 in the extended position, as shown in FIG. 1. As shown in FIGS. 2-3, the protective tip is operated into the retracted position, and the tissue 12 is pierced with the plurality of needles 30 such that their distal ends 34 are located on the distal side of the tissue 12. More particularly, the medical system is preferably oriented relative to the perforation 14 such that the needles 30 each pierce the tissue 12 around the periphery of the perforation 14. In other embodiments of the method, the needles 30 may pierce the tissue 12 and/or the tissue anchors 36 may be deployed prior to forming a perforation in the tissue 20. For example, an endoscopic cutting device may be deployed through the working channel 23 of the endoscope 22 and used to form the perforation within the boundaries defined by the needles 30 and/or tissue anchors 36.

Figure 6:
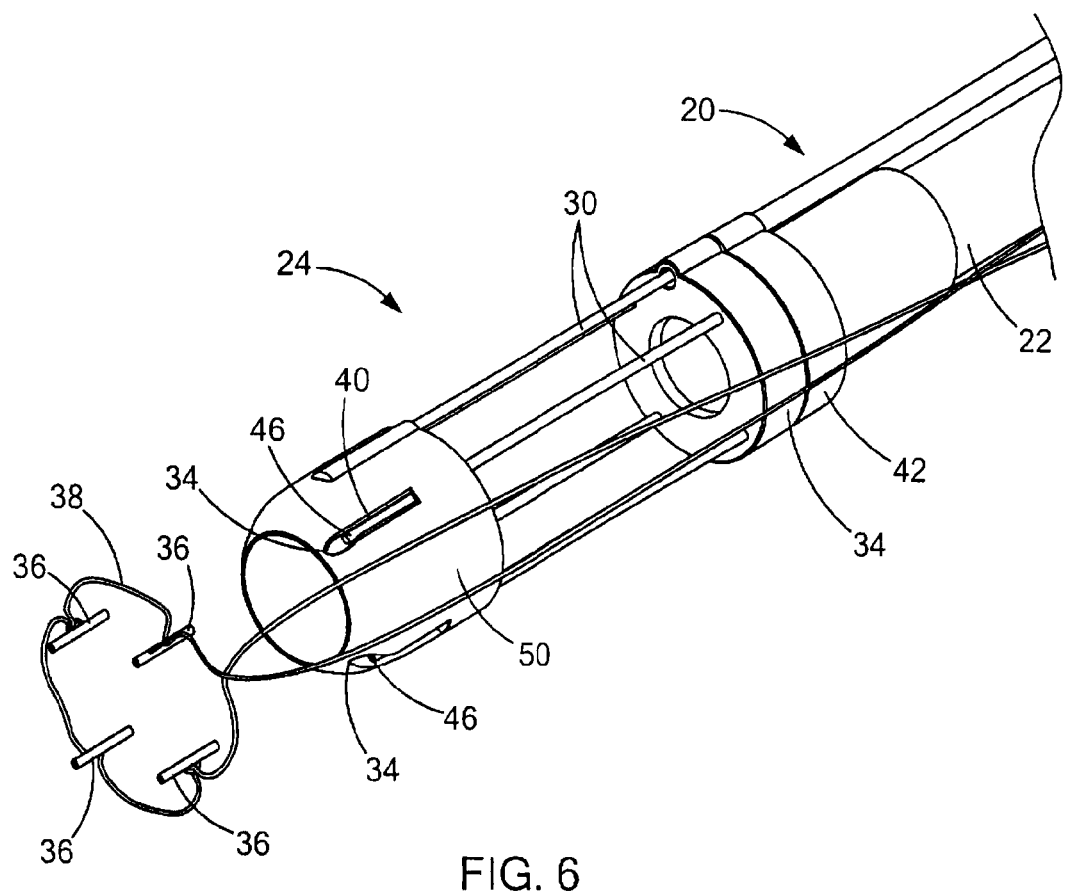
FIG. 6 is a perspective view showing still further operation of the medical device and system depicted in FIG. 1.
Figure 7:
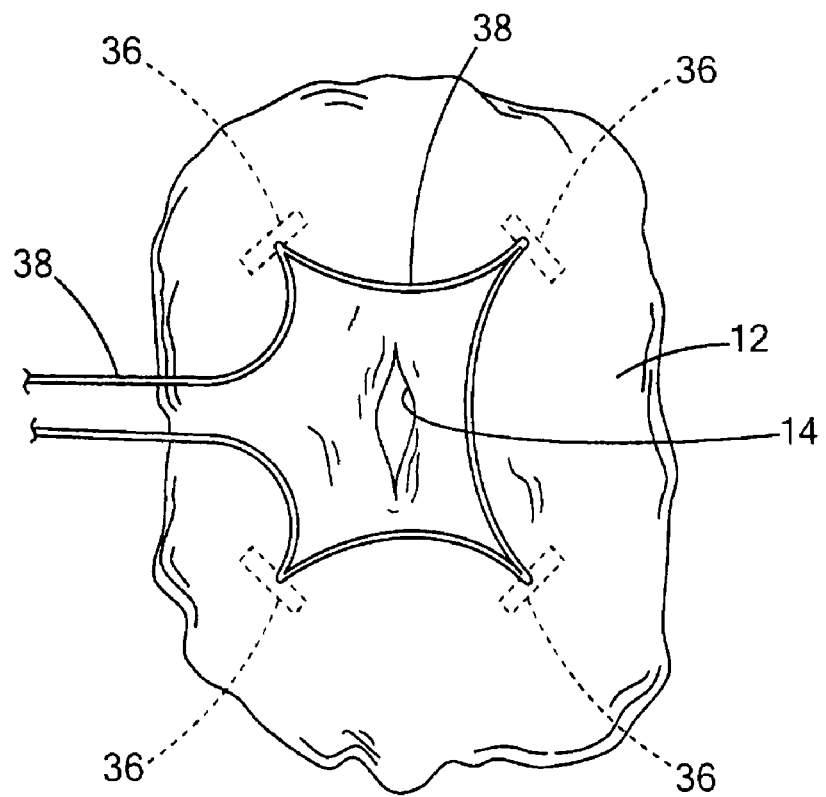
FIG. 7 is a plan view schematically depicting deployment of tissue anchors using the medical system and device depicted in FIGS. 1-6.
Figure 8:
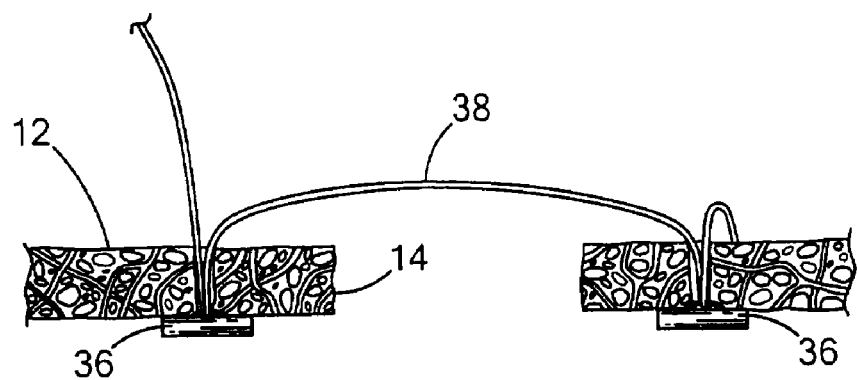
FIG. 8 is a cross-sectional view of FIG. 7.
Figure 9:
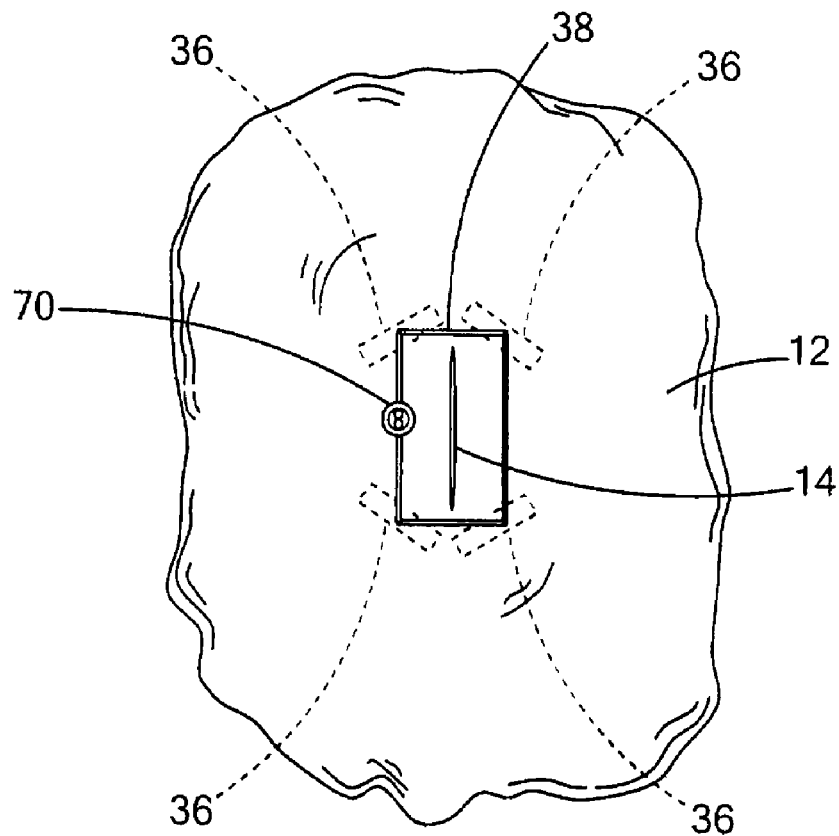
FIG. 9 is a schematic view similar to FIG. 7 showing closure of a perforation.
Figure 10:
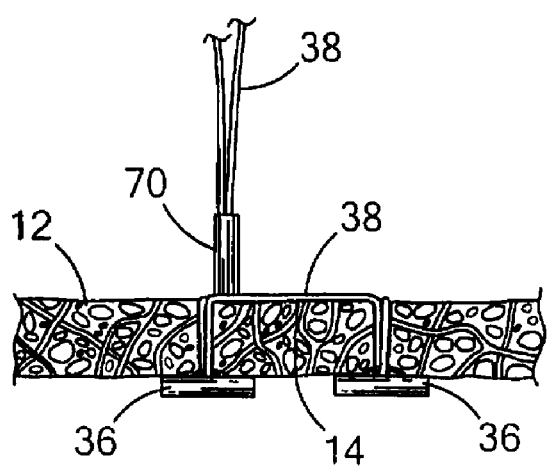
FIG. 10 is a cross-sectional view of FIG. 9.

As shown in FIGS. 4-5, the stylet cap 42 is translated relative to the endcap 26 to engage the plurality of tissue anchors 36 with the plurality of stylets 46 and deploy the tissue anchors 36 on the distal side of the tissue 12. The protective tip 50 may then be operated to the extended position, as shown in FIG. 6. Operation of the tip 50 may occur while the needles 30 are still in the tissue 12 (to help remove the needles from the tissue 12), or after the medically system 20 has been moved proximally to withdraw the needles 30 from the tissue 12. As shown in FIGS. 7-10, the suture 38 is slidably connected to each of the visceral anchors 36, leaving two free ends of the suture 38 that extend proximally through the bodily lumen and that may be independently tensioned to close the perforation 14. As best seen in FIG. 8, the visceral anchors 36 are positioned on a distal side of the bodily wall 12, while the majority of suture 38 is positioned on a proximal side of the bodily wall 12. The ends of the suture 38 are tensioned to reduce the distance between the visceral anchors 36 and compress the tissue 12 around the perforation 14, as depicted in FIGS. 9 and 10. As best seen in FIG. 10, the ends of the suture 38 are secured to maintain the compression of the tissue 12, such as through the use of a suture lock 70. Exemplary suture locks are disclosed in U.S. patent application Ser. Nos. 12/125,525 filed May 22, 2008 and 12/191,001 filed Aug. 13, 2008, the disclosures of which are incorporated herein by reference in their entirety. It will be recognized that any now known or future developed method for securing the ends of the suture 38 may be employed, such as knotting, tying, clamps, rivets and the like. The medical system 20 may be retracted through the bodily lumen with the protective tip 50 in the extended position (FIG. 6).

It will be recognized that during the methods of the present invention, the endoscope 22 may be used to visualize the procedures and operation of the medical devices and instruments. It will also be recognized that placement of the set of anchors 20 may be aided by fluoroscopy, ultrasound or visually through the use of medical instruments having imaging capabilities such as a fiber-optic catheter that is passed through the working channel 23 of the endoscope 22.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for use with an endoscope to manipulate tissue, the medical device comprising:
    an endcap having a passageway sized to receive the endoscope therein;
    a plurality of needles attached to the endcap and projecting distally therefrom, the plurality of needles defining a plurality of needle lumens and having distal ends for piercing tissue;
    a stylet cap slidably disposed over the endcap;
    a plurality of stylets attached to the stylet cap and projecting distally into the plurality of needle lumens; and a plurality of tissue devices positioned within the needle lumens, translation of the stylet cap relative to the endcap causing the plurality of stylets to engage the plurality of tissue devices and eject them from the plurality of needles.

2. The medical device of claim 1, wherein the plurality of needles are circumferentially spaced around the endcap.

3. The medical device of claim 1, wherein the plurality of needles are positioned radially outside of the passageway in the endcap.

4. The medical device of claim 1, wherein the plurality of needles includes at least four needles.

5. The medical device of claim 1, wherein the endcap defines a plurality of endcap passageways slidably receiving the plurality of stylets.

6. The medical device of claim 1, further comprising a protective tip slidably attached to the plurality of needles, the protective tip operable between an extended position protecting the distal ends of the plurality of needles and a retracted position exposing the distal ends.

7. The medical device of claim 6, further comprising a suture slidably attached to at least one of the tissue devices, the suture extending between each of the tissue devices around the exterior of the protective tip.

8. The medical device of claim 6, further comprising an elongated tip control member attached to the protective tip, and further comprising an elongated endcap control member attached to the endcap, and wherein the endcap control member defines a lumen slidably receiving the tip control member, relative translation of the endcap control member and the tip control member operating the protective tip between its extended and retracted positions to protect and expose the distal ends of the plurality of needles.

9. The medical device of claim 8, further comprising an elongated stylet control member attached to the stylet cap, wherein the stylet control member defines a lumen sized to slidably receive the endcap control member, relative translation of the stylet control member and the endcap control member operating the plurality of stylets to engage the plurality of tissue devices and eject them from the plurality of needles.

10. The medical device of claim 6, wherein the plurality of needles each have a length greater than the length of the protective tip.

11. The medical device of claim 6, wherein the protective tip defines a plurality of tip passageways slidably receiving the plurality of needles.

12. The medical device of claim 11, wherein distal portions of the plurality of tip passageways open laterally, and wherein the needles each define a laterally opening slot, and wherein the laterally opening portions of the plurality of tip passageways are circumferentially aligned with the laterally opening slots of the plurality of needles.

13. The medical device of claim 1, further comprising an elongated stylet control member attached to the stylet cap, and further comprising an elongated endcap control member attached to the endcap, and wherein the stylet control member defines a lumen sized to slidably receive the endcap control member, relative translation of the stylet control member and the endcap control member operating the plurality of stylets to engage the plurality of tissue devices and eject them from the plurality of needles.

14. The medical system of claim 1, wherein the distal ends of the plurality of needles are positioned distally beyond the distal end of the endoscope and a distal end of the endcap when the medical device is fitted on the endoscope.

15. The medical system of claim 1, wherein the endcap defines a flange extending radially outwardly, the flange sized and positioned to abut the stylet cap to limit the relative translation of the stylet cap and the endcap.

* * * * *